United States Patent [19]

Erickson

[11] Patent Number: 4,781,686
[45] Date of Patent: Nov. 1, 1988

[54] AUTOMATIC SAFETY VALVES FOR CARDIOTOMY RESERVOIRS

[76] Inventor: Oscar A. Erickson, 2051 Ridgeview Ave., Los Angeles, Calif. 90041

[21] Appl. No.: 62,396

[22] Filed: Jun. 15, 1987

Related U.S. Application Data

[63] Continuation of Ser. No. 367,908, Apr. 18, 1982, abandoned.

[51] Int. Cl.[4] .................................................. A61M 1/00
[52] U.S. Cl. .................................................. 604/118; 137/540
[58] Field of Search .................................. 604/4–9, 604/317, 318, 118, 119; 137/540, 514; 220/202, 203, 209

[56] References Cited

U.S. PATENT DOCUMENTS

| 401,391 | 4/1889 | Stuck | 137/540 |
| 3,157,191 | 11/1964 | Garrett et al. | 137/540 |
| 3,192,949 | 7/1965 | DeSee | 137/540 |
| 3,782,412 | 1/1974 | Davesh | 137/514 |
| 3,993,067 | 11/1976 | Schachet | 604/9 |
| 4,328,828 | 5/1982 | Ciani | 604/317 |

FOREIGN PATENT DOCUMENTS 466192 5/1914 France .................. 137/540

OTHER PUBLICATIONS

'ITHAT' Catalog Cut. Medi-Vac Corp. Jacksonville, Texas 75766, 1979.

Primary Examiner—Stephen C. Pellegrino
Assistant Examiner—J. L. Kruter
Attorney, Agent, or Firm—Fleit, Jacobson, Cohn & Price

[57] ABSTRACT

A safety lock cap for use with a cardiotomy reservoir, having a passageway formed therein under control of a positive pressure relief valve and projecting axially into the reservoir beyond the outer tubular portion of the cap inserted into a port opening in the reservoir vessel. Under positive pressure, the cardiotomy reservoir is vented through the passageway so that during operation of a heart-lung machine the safety lock cap will provide a minimum amount of safe positive pressure and become a relief valve that decompresses the cardiotomy reservoir.

11 Claims, 5 Drawing Sheets

U.S. Patent    Nov. 1, 1988    Sheet 1 of 5    4,781,686
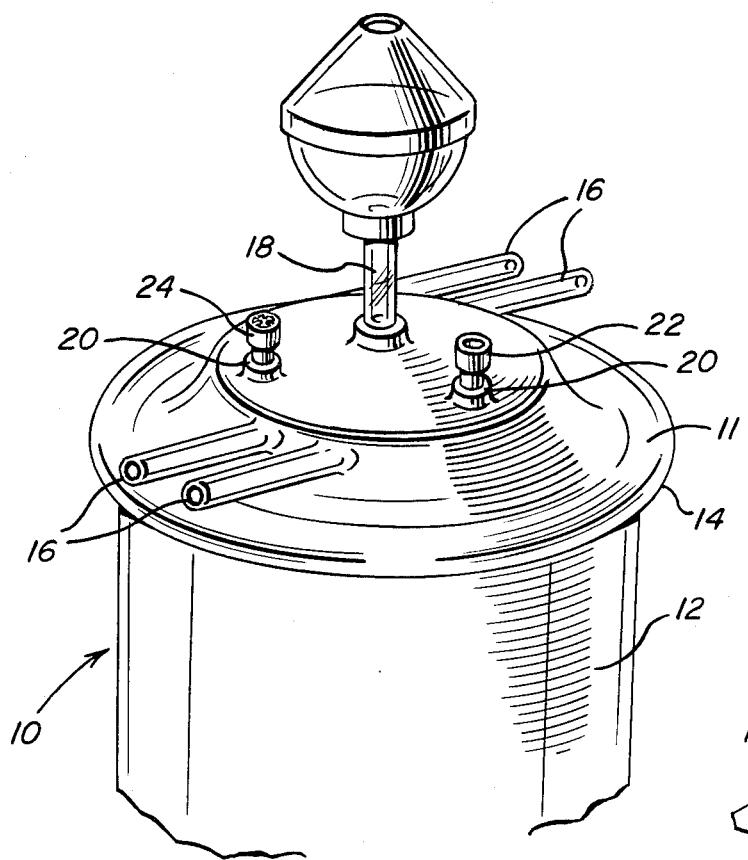
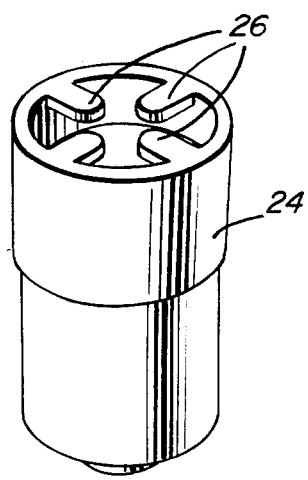
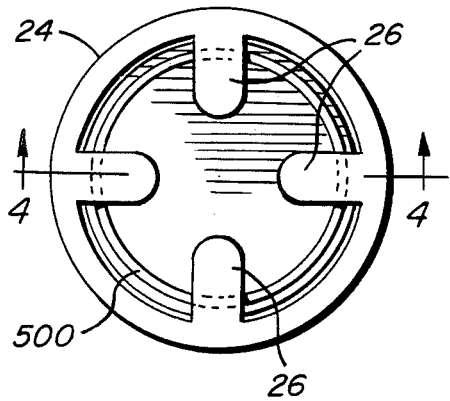
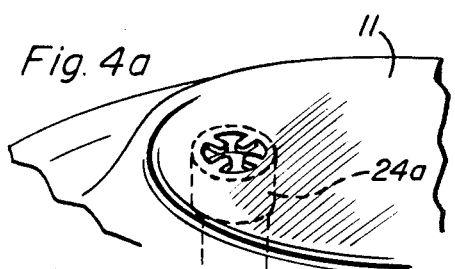

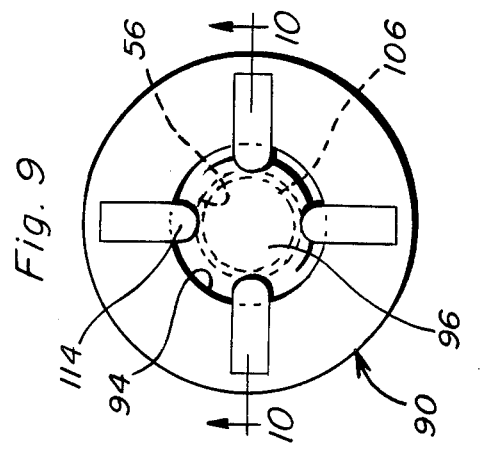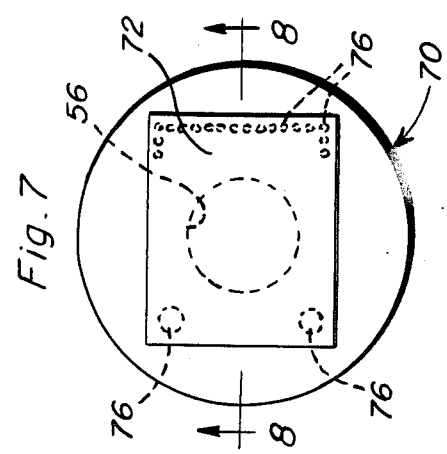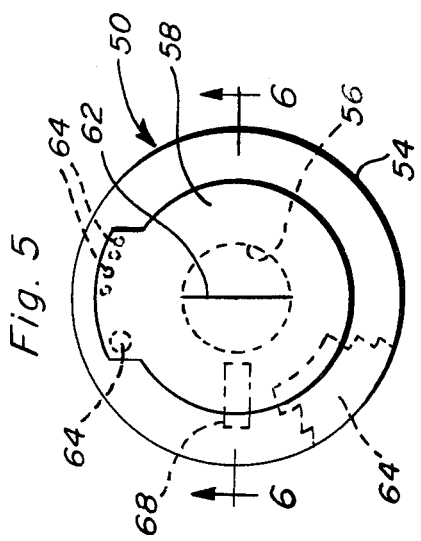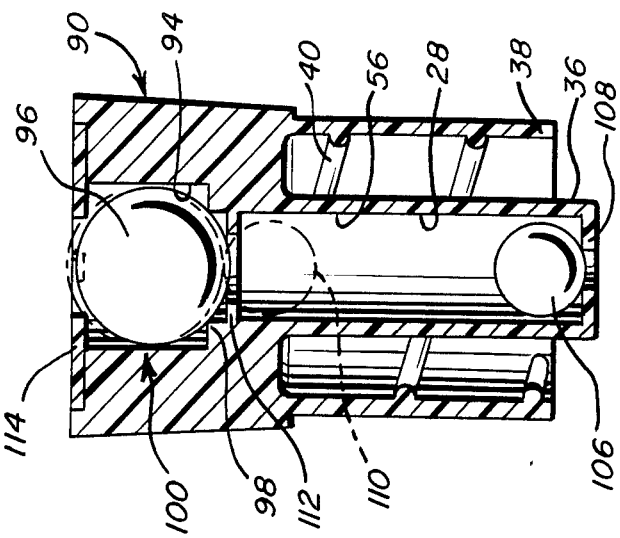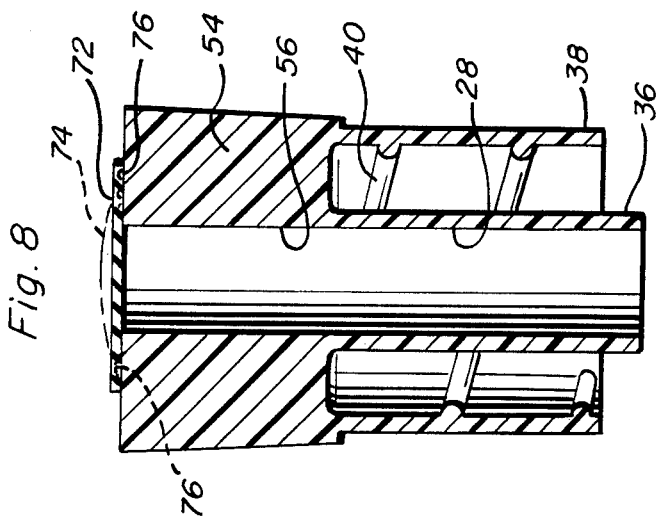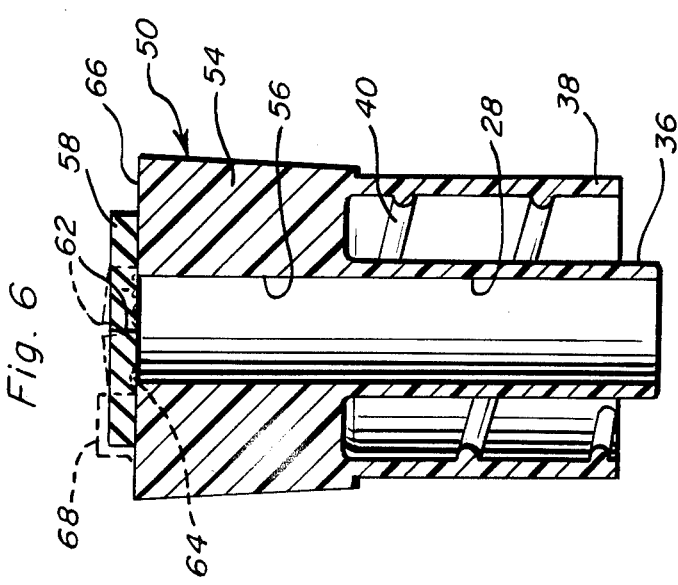

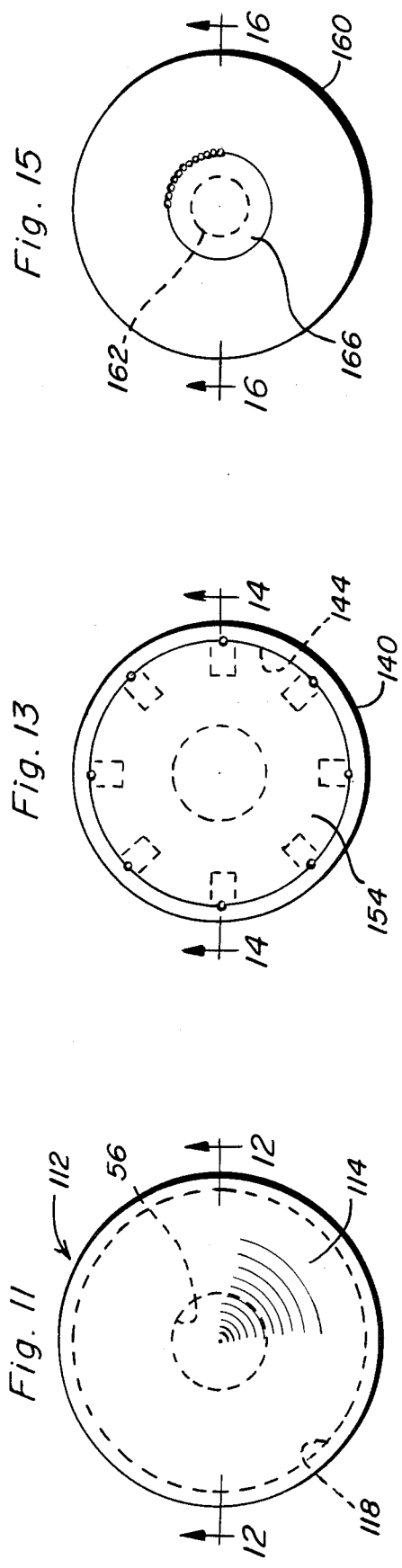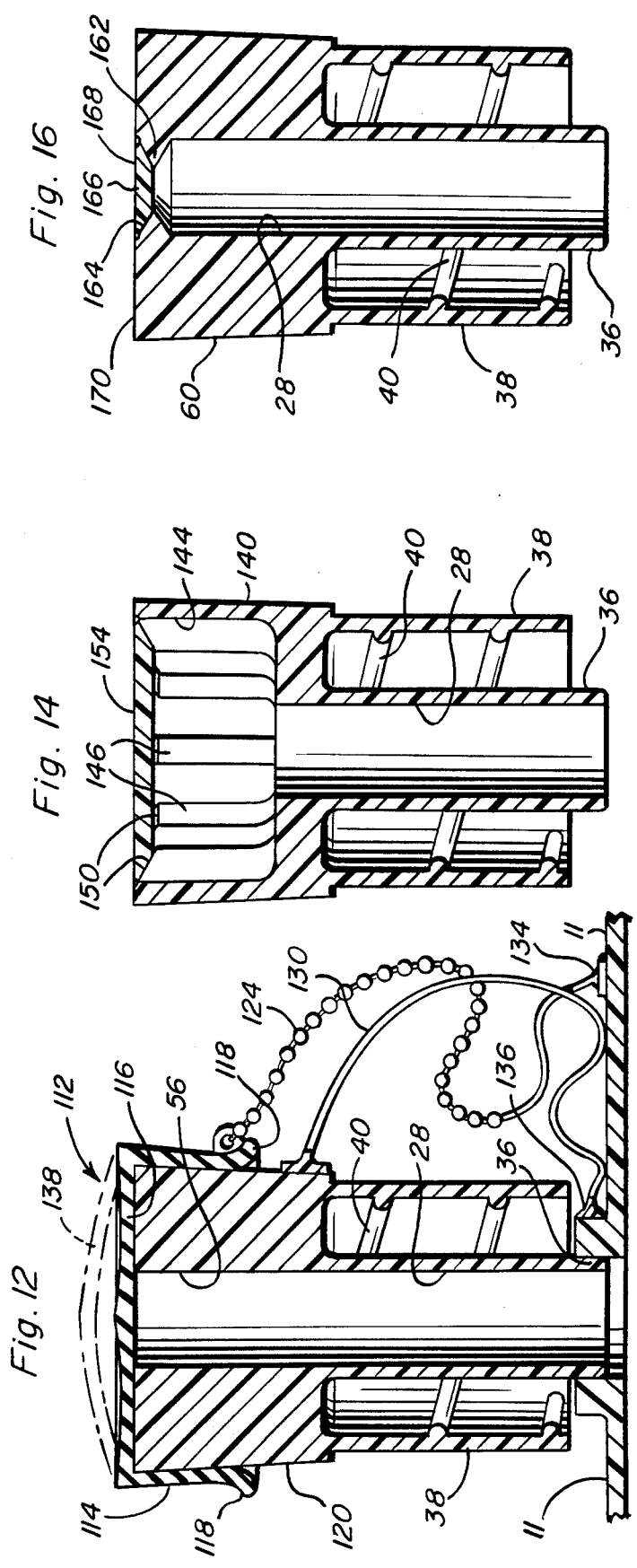

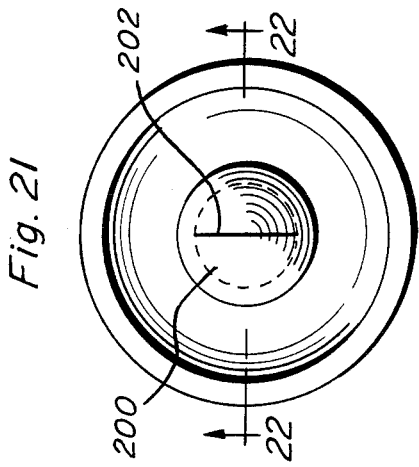
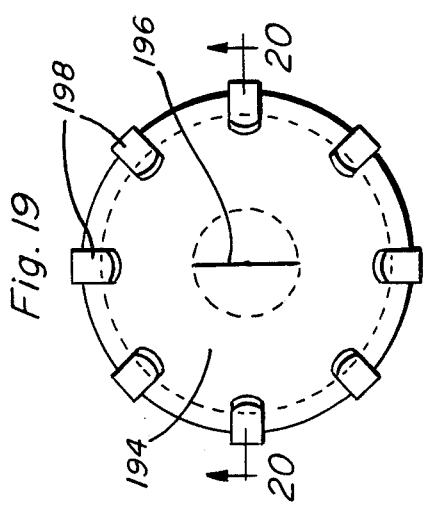
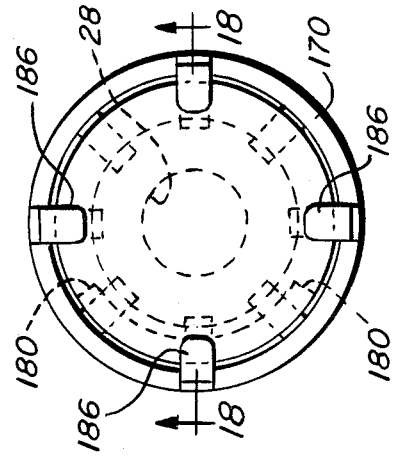
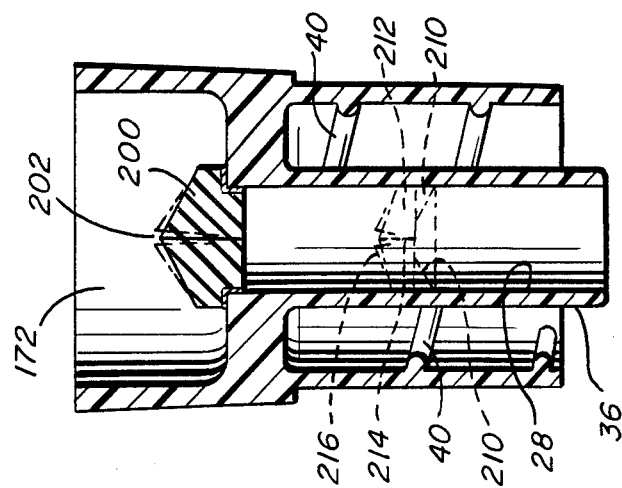
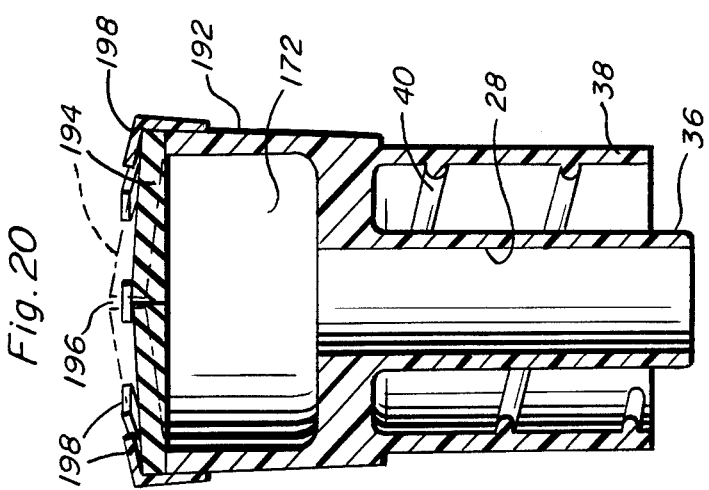
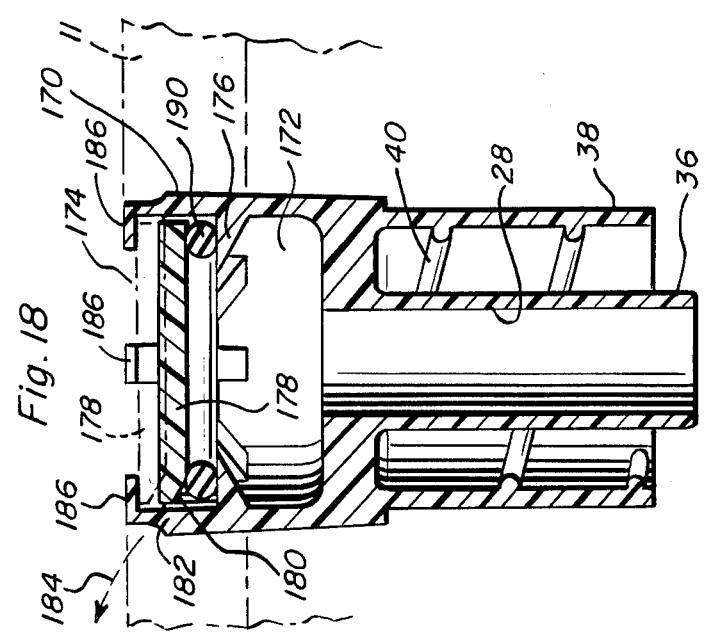

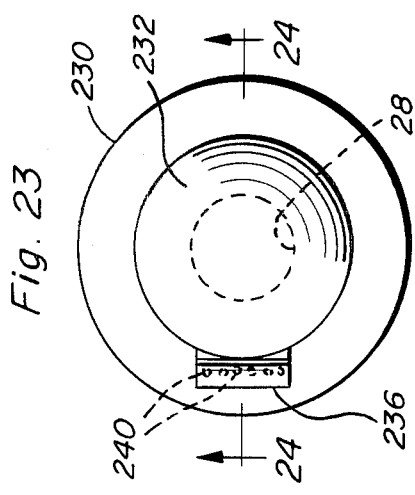
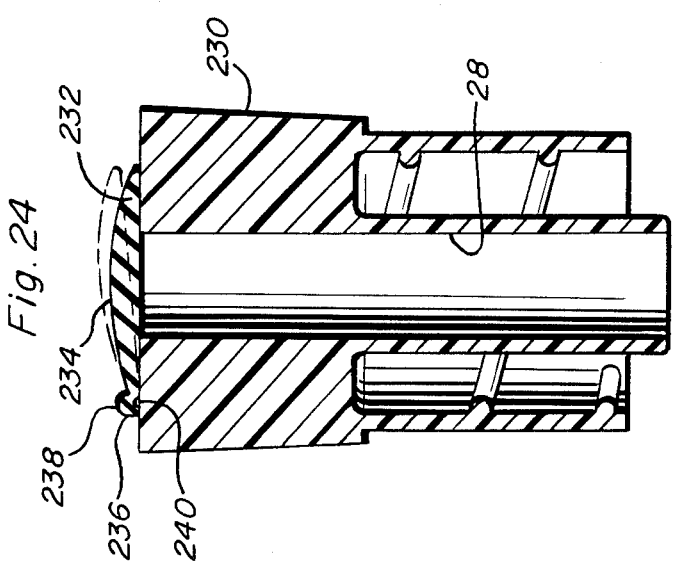
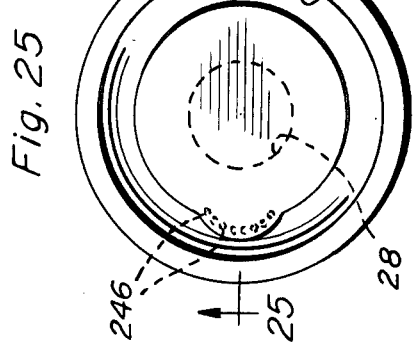
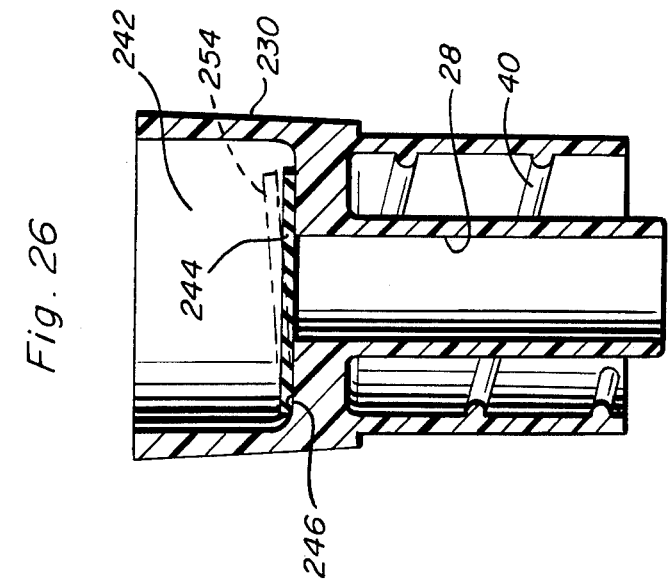
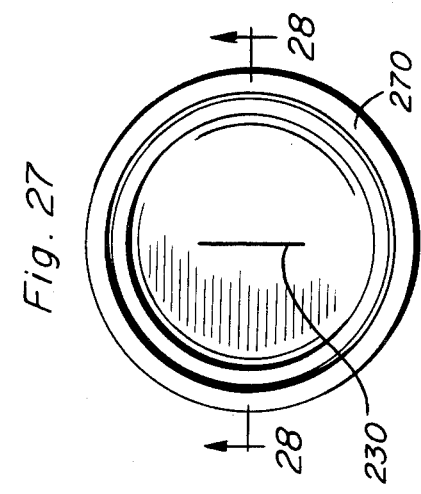
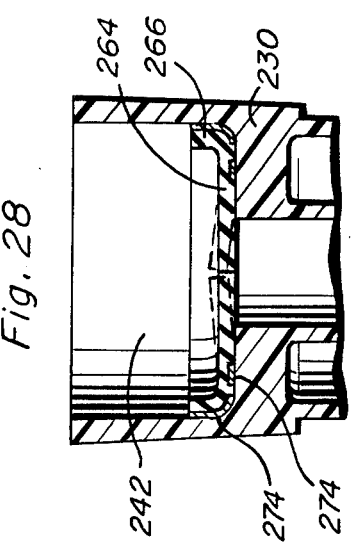
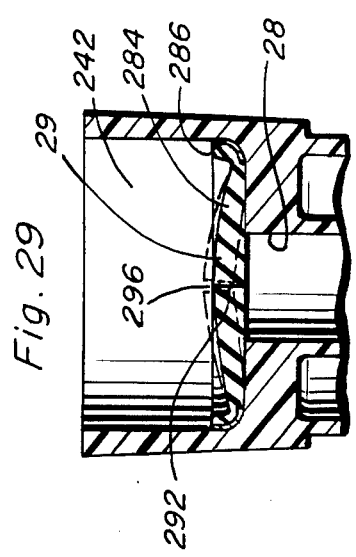

AUTOMATIC SAFETY VALVES FOR CARDIOTOMY RESERVOIRS

BACKGROUND OF THE INVENTION

The present application is a continuation of U.S. Ser. No. 367,908 now abandoned, disclosing an invention which relates to a construction for a cap and valves applied to a lid cover of a cardiotomy reservoir so that the positive pressure in the cardiotomy reservoir is vented and decompresses the cardiotomy reservoir thus preventing overpressurized cardiotomy reservoirs.

More particularly, the invention relates to providing metal, plastic, frangible material and foam rubber type constructions for a lock cap which has an opening bored therethrough so that positive pressure values within the cardiotomy reservoir are relieved.

During use of heart-lung machine apparatus during the course of operations such as cardio-pulmonary bypass operations, normal operating pressure values within a cardiotomy reservoir are generally negative or at a pressure which are the same as atmospheric pressure. However, pressures greater than atmospheric pressure are abnormal if too high. The cardiotomy reservoir is connected together with a filter in shunt relation to an oxygenator and its arterial reservoir. Where such filter is located downstream of the cardiotomy reservoir and the reservoir filter becomes clogged or cardiotomy return line is clamped or occluded, excess pressures or positive pressures build up within the cardiotomy reservoir and may improperly be released within the patient by way of an arterial line, causing air entry into the patient's aortic cannulae, then to the aorta, the carotid arteries and finally to cerebral arteries and possibly causing what is commonly referred to as a "brain death". This occurs where a lock cap such as a "Luer-Lock" cap or other port caps improperly remain in closed condition on the lid cover of the cardiotomy reservoir. Failure to remove such air lock cap is presumed to have caused loss of a patient's life during a cardio-pulmonary bypass operation due to an overpressurized cardiotomy reservoir. Where one has not become fully familiar with all of the facts and operation as to the etiology of such a system, it has become known that a downstream cardiotomy reservoir filter had possibly become clogged. The suction mode was that of roller head from the operating table to the cardiotomy reservoir and it may become quesitonable if the head setting was occlusive or non-occlusive. The arterial line filter was shunted to a non-vented cardiotomy reservoir and what would be ensued in summarization is that the air pressure within the cardiotomy reservoir exceeded atmospheric pressure (760 Mm.Hg.) and hydrostatic pressure causing the filter shunt to become filled with air which forces the air into the arterial filter and up to the patient via the arterial line, venous line, sump or vent line.

Various methods and apparatus are now in use without any recommended safe practice fully adopted that would preclude an arterial filter shunted to a non-vented reservoir or with a vented reservoir other than the venous inlet of some oxygenator. It may not be fully clear how a downstream-in-line cardiotomy return filter may become clogged or how it becomes defective, or whether the Heparin dose was adequate, or were roller heads occlusive or non-occlusive which could have created another problem. While various measures are clear in retrospect, such as routinely removing a lock cap from the cover of the cardiotomy reservoir to drop the reservoir pressure, it is also possible to use a manufactured purge line with a one-way valve that allows one-way shunting of fluids and air. Further, considering a possibility that purge lines may be used, compressed air may have caused an explosion with use of an overpressurized reservoir with no escape for the high pressure.

Various forms of closure caps are known which effectively provide for a release of pressure in a sealed structure in the event that such pressure exceeds a predetermined level. It should be appreciated that the pressure relieving valve in automatically exercising its function within such prior art closure caps must do so without adversely affecting the pressure sealing fit of the cap within the tubular port opening in the reservoir vessel. Such sealing fit is usually achieved by contraction of the outer tubular portion of the cap when inserted into the tubular port opening. Thus, an important aspect of the present invention is to provide automatic overpressure relief without disturbing the cap sealing fit or the seal maintenance action of the reservoir pressure.

A further object of the present invention is to provide a safety cap and relief valve device usable on a heart-lung and auto transfusion type machine such as used during open-heart and other surgery and for providing thereby positive pressure relief for allowing decompression of the cardiotomy reservoir.

Yet another object of the present invention is to provide teaching for modification of prior art safety caps for venting a cardiotomy reservoir under positive pressure as well as under negative pressure maintained without loss.

SUMMARY OF THE INVENTION

In accordance with the present invention, a cap structure which is insertable into a port opening of a reservoir vessel has an outer cylindrical portion radially spaced from an inner cylindrical portion to form thereabout an annular chamber pressurized by the fluid in the reservoir in order to maintain the sealing fit of the cap body within the port opening. A vent passage controlled by a pressure relieving valve extends axially beyond the pressurized annular chamber into the reservoir so as to apply the automatic pressure relieving action of the valve to a fully opened end of the vent passage axially spaced from the annular chamber. Thus, the reservoir pressurized annular chamber seals the cap despite the overpressure relief function associated therewith. The annular chamber is essential in order to accommodate elastic contraction of the outer tubular portion of the cap and internal pressurization thereof, while the establishment of the vent passage within the inner portion is achieved in accordance with the present invention by fully opening the projecting axial end of the inner portion, contrary to the prior art, for communication with a valve-controlled vent chamber formed within the upper body portion of the cap.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of one type of cardiotomy reservoir as used in conjunction with the present invention.

FIG. 2 is a perspective view of a cap.

FIG. 3 is a plan view of the cap of FIG. 2.

FIG. 4 is a sectional view of the cap of FIG. 3 taken along lines 4—4 thereof.

FIG. 4-A is a fragmental perspective view of a cap or valve device integrally constructed within a lid cover, body, shell, or existing port, above the expected fluid level of a cardiotomy reservoir.

FIGS. 5–29 are respective plan and sectional elevation views of caps embodying different versions of the present invention.

DESCRIPTION OF THE PREFERRED EMBODIMENTS

Referring now to the drawings, there is shown in FIG. 1 a cardiotomy reservoir 10 with a lid cover or shell body such as used in an extracorporeal circuit (not shown) during open-heart procedures and as used in utilizing heart-lung machines or auto transfusion devices (not shown). The reservoir 10 has hydrostatic level markings 12 for fluids or blood during use thereof. A lid having a median flange 14 for mounting on the reservoir, is provided with a set of four ports 16 for connection to suction lines through filter and defoamer units, a rapid prime port 18 for coupling through a defoamer unit (not shown) which is what may be used for left ventricular vent blood and solutions that do not require microaggregate filtering, and a set of at least two luer ports 20 for coupling through filter and defoamer units for the addition of bank blood. Two luer ports 20 are provided so that during operation of suction line pumps (not shown) connected in line with these luer ports 20, one of the parts or ports 16 may be used as an air vent or it may be used to add fluid into the reservoir if the luer lock fitting directly opposite on the same perimeter is open. Blood flowing to the oxygenator can be adjusted by raising and lowering the adjustable cardiotomy reservoir holder (not shown).

Luer ports 20 are provided with luer-lock caps 22, 23, cap 22 closing off the port 20 as shown and the cap 24 being modified as shown in FIGS. 2–4 so that there is a strut or cage structure 26 at the upper or open end of the cap body and an inner cylindrical tube 36 at the other end of the body through which a passage or bore 28 extends axially from free space 30 within the cage 26 to the lower extremity of the cap. An annular space 34 between cylinder 36 and an outer cylinder portion 38 of the cap has an internal helical thread formations 40.

As is already well known with respect to luer-lock caps, the annular chamber 34 enables the outer cylinder portion 38 which has an internal helical thread 40 so that the outer cylindrical portion will thereof be contracted under compression during insertion of the cap into a port 20. The inner cylinder portion 36 of the cap projects axially beyond the chamber 34. In accordance with the present invention, the axially projecting end of the hollow inner portion 36 of the cap is fully open by a vent passage bore 28. Within the bore 28 there is a T-shaped valve 44 of generally circular configuration resting upon a valve face 46 within the cage 26 and free space 30. Pressure displaces the T-shaped valve upwardly as shown by arrow 47 when the pressure within the cardiotomy reservoir 10 is positive. The T-valve tends to be gravitationally displaced downwardly as shown by arrow 47 when the pressure within the cardiotomy reservoir 10 is negative.

A spring 500 is disposed within space 30 in abutment with cage 26 and valve element 44 to bias the valve element in a valve closing direction into contact with valve seat face 46.

Various modifications of the vent cap embodiment shown in FIGS. 3 and 4 are contemplated. For example, the valve element 44 may be provided with an upper surface portion flush with or projecting above the top of the cap 24 through the cage 26 to enable one to depress the valve element so as to optionally maintain overpressurization. The cage 26 is such case would prevent disassembly of the valve element from the cap, upon release of the valve element, because of a large buildup of pressure prior to release. Facilities may also be provided to establish an audible alarm in response to escape of air from the cap as a result of overpressurization within the cardiotomy reservoir. Further, the body of the vent cap may be made integral with the lid cover 11, as shown in FIG. 4A with respect to cap 24a. In all cases, the valve element 44 is made of a radiated, autoclavable material.

A safety luer-lock reservoir cap 50 shown in FIGS. 5 and 6 includes a cap body 54 provided with a driller hole or aperture 56 extending through the entire length of the cap 50 so that it cooperates with a unidirectional valve body 58 having a slit 62 extending partially across a diametrical region of the valve body 58. The valve body 58 may be glued at one edge along a radial portion 64 of the surface 66 of the cap and secured thereto by a glue or it may be held with augmented struts or ring attachment 68. The attachment 68 may be incorporated in and molded as part of the cap, or it may be separately constructed and added to the cap structure. The slit 62 acts as a valve release when positive pressure is present in the cardiotomy reservoir 10 and closes when negative pressure is present. The material of valve body 58 may be autoclavable, etc, radiation and steam-proof or steamable material, and may be of sponge material, sponge rubber, plastic paper-like material, or sponge metal material as approved and usable in this art.

A safety luer-lock reservoir cap 70 shown in FIGS. 7 and 8 is provided with a valve body 72 thinner than the valve body 58 of FIGS. 5 and 6, the valve body 72 being shown as generally rectangular and expansible to a position indicated by dotted lines 74 when positive pressure is present within the cardiotomy reservoir 10. It is within the purview of this embodiment of the invention to utilize and valve bodies of different configurations, including circular, octagonal, triangular, and letter-shaped, such as T, C, S, H, B-D, and the like. Such valve bodies may secure to the top of the cap body 54 by various attachment methods such as a series of spot glue points 76 shown in FIGS. 7 and 8. Test on this construction releases air with a whistle sound when the positive pressure above 80 mm. Hg. is present in the cardiotomy reservoir.

Configurations of the safety luer-lock reservoir cap 90 shown in FIGS. 1, 9 and 10 embodying a cap body that is modified so that the internal aperture 54 is enlarged at its upper end to an aperture 94 for receiving a ball valve member 96 for resting against a valve face 98 forming a first valve assembly 100. Alternative or in conjoint relation with the valve assembly 100, there is provided a separate ball 106 cooperating with a valve face 108 which is displaced when positive pressure in the cardiotomy reservoir is sufficient to overcome the normal position of the valve ball 106 and its residual force due to gravity whereupon the presence of adequate positive pressure within the cardiotomy reservoir may be sufficient to displace the ball 106 upwardly as shown by dotted line 110. The ball 110 in position as shown is retained in the space by means of struts or extensions 112, and similarly the ball 96 is retained in place by struts or cage elements 114. Thus there is shown two configurations of a ball valve assembly where either ball 96 or ball 106 with associative circular retainer elements 108, 112, 114 are provided to seal the ball in position and for the valve to perform as a relief valve under certain positive pressure values. An embodiment of a safety cap 112 illustrated in Figs. 11 and 12 is provided with a safe physiologic pressure blow off cap 114 having a central frangible member 116 extending across the aperture 56 while there are side extensions of lips 118 extending downwardly along a truncated conic surface 120 as shown. More particularly, there is shown in FIG. 12 a restraining member 124 that prevents the reservoir cap 112 from becoming irretrievably displaced and lost, which circumstance avoids causing distal removal of the valve cap 114 under positive pressure conditions within the aperture 54, so that the cap can be availably replaced upon the cap and surface 120. Also, similar retention or restraining member 130 is provided preventing distal displacement of the cap itself, each of the members 124, 130 secured to the lid cover 11 at terminal ends 134, 136 as shown. These terminal ends 134, 136 may be secured by glue means, such as described above in connection with securing the valve body onto the valve cap as described. Upon positive displacement of the central portion of the valve cap, FIG. 12 shows that it is capable of being distended to the dotted line 138. In FIGS. 13 and 14, there is shown an arrangement for a cap 140 provided with an enlarged space 144 having a series of ribs 146 converging into the aperture 28 at the lower extremity and having inclined surfaces 150 at their upper extremity for receiving a plastic lid 154 for forming the valve, the lid 154 secured by glue means to the upper surfaces 150 of the ribs 146 and in this way provide a fracture ventilating release valve upon excessive positive pressure present within the aperture 28 and the cardiotomy reservoir 10. This form of valve assembly seals under negative pressure and fractures upon upon positive pressure performing as a relief valve.

A comparable arrangement of a safety cap valve assembly is shown in FIGS. 15 and 16 in which the cap 160 is provided with a substantially continuous aperture 28 until it reaches an internal projection 162 forming upon its upper inclined surface 164 a valve engaging surface for the valve body 166, having a flat surface 168 on one side thereof coplanar with surface 170 of the safety cap 160 while the other surface resembles a truncated cone configuration for engaging the surface 164. Similarly, the valve opens upon positive pressure conditions within the aperture 28 and the cardiotomy reservoir 10, the configuration of the valve in FIGS. 15, 16 being of a smaller and reduced size of the valve assembly of FIGS. 13, 14.

In the configuration of FIGS. 17, 18, a safety cap 170 and a lid cover 11 has a central aperture 28 opening into a larger cavity 172 and communicating with an open space 174. The cavity 172 contains an annular member 176 contoured as an inwardly extending flange for supporting a cover lid 178 constituting a sealing or closure disk member continuous with the diameter of the cavity 172. A chamber portion 180 of the disk provides escapement passage for positive pressure contained within the aperture 28 and cavity 172, and in which the lid cover 178 is driven upward to the dotted line configuration of the lid cover 178 as shown in FIG. 18 and thus escapement of air is directed through an aperture 182 as shown by the arrow 184. For retaining the cover lid into the cavity 172, there are provided a plurality of struts 186 for limiting the upward displacement of the cove lid 178, the upward displacement being shown in the dotted line configuration of lid cover 178 in FIG. 18. For assuring increased sealing efficiency and effect, a soft resilient elastomeric O-ring 190 is provided inbetween or interpositioned between the annular flange 176 and the cover lid 178 so that upon ambient or negative pressures within the cavity 172, the aperture 28 as well as the cardiotomy reservoir 10, secure closure achieved by the O-ring 190 cooperating with the lid over 178 and flange 176. This effect and operation is also achieved in other seals disclosed herein and above by which the material chosen to constitute the seal or closure readily conforms to the mating structure formed about a cavity or adjacent areas about the aperture 28.

FIGS. 19 and 20 show a cap 192 having a cavity 172 covered by a partially slit disk 194 and in which the disk is provided with a slit 196 extending about 1/4-1/3 of the total diameter of the disk 194. The disk 194 is retained in position by struts 198 affixed to the peripheral surface of the cap 192 and formed over the disk 194. The presence of positive pressure within the cavity 172 asserts expansion of the disk 194 so that it is generally distorted upwardly as shown by the dotted line configuration of the disk 194 and the slit 196 opens for the escapement of positive pressure within the cavity 172.

A similar configuration is shown in FIGS. 21 and 22 in which the cavity 172 contains the entire seal member 200 having a slit 202 extending about 7/8this the distance of the diameter of the seal 200 and, due to the contour shown, the effective surface forming this seal is vastly increased due to the peaked effect of the slit 202 extending from the peak of the seal 200 down to the lower extremity thereof and the effect of the seal under ambient and negative pressures assures that a positive seal under these ambient and negative pressures assures that a positive seal under these conditions, but under the presence of a positive pressure within the aperture 28, the seal 200 performs as a positive release also due to the construction of the slit 202. While the valves that are described and disclosed in FIGS. 1-22 are all a seal or valve configuration generally small in structure and dimensions, these valves sometimes being called "Valvules" or "Valvelets" an even smaller type of valve is schematically shown in dotted lines within the aperture 28 of FIG. 22 and in which there is provided an annular internally extending flange member 210 extending around the interior of the aperture 28 for supporting a small valve or seal member 212 having a slit 214, it being shown in an open condition by the open slit 216. The function and operation of the seal 212 resembles that of the operation of seal 200 described above. These valves and seals, or Valvelets are a unidirectional or one-way relief valve sealed closed under negative and ambient pressure conditions, but are blown open with positive pressure within the cavity or aperture 28, thus relieving positive pressure conditions within a cardiotomy reservoir or otherwise release of excessive extra corporeal biological pressures.

FIGS. 23-26 show a cap 230 constructed of metal or polymer material such as polycarbonate plastic of different colors, for color coding purposes, such as red, blue, orange, or green. The cap 230 is provided with the aperture 28 for opening the entire length along the axial dimension of the cap, and in this connection it is possible to use conventional luer-lock caps and having them opened up completely by forming the aperture 28. The closure 232 of FIGS. 23 and 24 may be of an elastomeric material such as silicone or latex rubber and may be of any colors, the closure being of generally circular configuration and having a small dome 234 effect to the cover 232. Along one point of the cover there is a hinge structure 236 which also possesses a rise 238 for forming the hinge 236 and it is secured in mating relation with the fault surface of the cap 230 by a plurality of glue spots 240 for forming cohesive forces between the cover 232 and the cap 230. In this way each of the component parts may be separately molded or it is contemplated that the entire assembly may be integrally molded and thus forming a living-type hinge 236 where it is formed integrally with the cap 230. Where a common or integral mold process is performed, a cut operation or step is provided to sever the cover 232 along its entire surface from the cap 230 up to the point where the hinge 236 is preserved. This provides a sure closure since the materials have been integrally formed and constructed onto or within lid 11. The arrangement of FIGS. 25 and 26 provide a closure recessed within a cavity 242 and in which the closure 244 is generally flat but circularly contoured and having an arcuate arrangement of glue spots 246 formed in such a way that the arcuate contour of the glue spots 246 bias the cover 244 into a closed and sealed relationship until positive pressure exists within the aperture 28 which then is dissipated by opening the cover 244 to its position shown as 254 in dotted line.

A different arrangement is shown in FIGS. 27 and 28 in which the cap 230 with its recess 242 is provided with a disk-shaped closure seal 264 having upwardly extending lip 266 projecting from the generally flat contour of the seal 264 and in which it is yet contoured for filling the contour formed by the cavity 242. The seal 264 is constructed to contained a partially diametrical slit 270 extending in a given direction and the seal 264 is glued by a series of spots 274 in a direction transverse to the slit 270 as shown in FIG. 28. FIG. 29 shows a similar seal 284 having an upwardly extending lip 286, the contour of the seal 284 being essentially congruent throughout its contacting surface with the cavity 242 and the seal having a dome-shaped configuration 290 so that there is a partially diametrical cut or slit 292 similarly extending about one-third of the diametrical distance across the entire cap. When the slit is open it is in the positions of slit 296 shown in FIG. 29 and due to the dimension of the slit along the axial orientation of the cap, the seal is found to provide improved sealing effect under negative and ambient pressures prohibiting any leakage or escapement of gas into the aperture 28, but the slit readily opens providing escapement of positive pressures from the aperture 28.

The several embodiments of this invention are provided with an alarm or alertment of the escapement of positive pressure when these valves or seals are constructed to allow a whistle effect or swish of air passing through the seal or valve member. Otherwise, the seal or valve of the safety cap 10 is securely closed under ambient and negative pressure conditions within the cardiotomy reservoir 10, but when the whistle or sound effect is desired to alert an alarm when positive pressure is contained therein, the caps are usable as an audible alarm system evident by sounds of the whosh or the acoustic affect provided by the ball member, the slit providing passage of air escapement, and the like, and this condition prevails until over pressurization within the system is reduced. When such noise does exist in the system, it is possible for an operator to completely remove the safety cap which he may do under conditions suitable for use of the system.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. In combination with an internally pressurized reservoir having at least one port opening and a cap closing said port opening, said cap including an outer cylindrical portion inserted into the reservoir through said port opening with a sealing fit having an internal helical thread, a body portion connected to said outer cylindrical portion in axially spaced relation to the reservoir and an inner hollow portion projecting axially from the body portion in radially spaced relation to the outer cylindrical portion forming an annular chamber therein pressurized by fluid from the reservoir to maintain said sealing fit, said inner portion having an axial end projecting beyond the outer cylindrical portion into the reservoir, said body portion enclosing a vent chamber therein, said inner portion being fully opened at said axial end thereof and having a vent passage of uniform flow area extending between said fully opened axial end and the vent chamber, positive pressure opening valve means rendered operative for automatically relieving excessive pressure within the reservoir and valve seat means mounting the valve means on the body portion in fluid communication with the vent passage for rendering the valve means operative in response to said excessive pressure developed at said fully opened axial end of the inner portion within the reservoir axially spaced from the annular chamber without affecting said pressurization thereof.

2. The improvement as defined in claim 1 wherein the vent chamber extends radially beyond the vent passage in communication therewith.

3. The improvement as defined in claim 2 wherein said valve means includes a valve seat surface formed within the vent chamber and a valve element engageable with said valve seat surface.

4. The improvement as defined in claim 3 including cage means mounted on the body portion of the cap for retaining the valve means within the vent chamber.

5. The improvement as defined in claim 2 wherein said valve element includes a stem portion projecting into said vent passage.

6. The improvement as defined in claim 5 including cage means mounted on the body portion of the cap for retaining the valve means within the vent chamber.

7. The improvement as defined in claim 1 wherein the body portion of the cap has an axial end surface, said valve means cooperating with the cap for controlling flow through said vent passage under negative and ambient conditions within the reservoir to release physiologically dangerous positive pressures within the reservoir.

8. The invention of claim 7 wherein the valve means is made of the material from a class consisting of plastic, rubber, sponge, spongelastomeric, foam rubber sponge, sponge metal, the valve means being operable to vent positive pressure from the reservoir, thus preventing overpressurized conditions in the reservoir.

9. The invention of claim 7 wherein the valve means comprises an axially displaceable disk and caging means for retaining the disk within the body portion of the cap comprising a set of peripheral struds.

10. The invention of claim 9 wherein the valve means further includes a T-shaped head portion received in the vent chamber and a stem projecting therefrom into the vent passage, the body portion of the cap having a plurality of struts extending radially inward of the vent chamber.

11. In combination with an internally pressurized reservoir having a port opening, a cap having an outer tubular portion received in said port opening with a sealing fit and enclosing an annular chamber pressurized by fluid from the reservoir, a helical thread internally mounted on the outer tubular portion exposed to and projecting into said chamber, valve means carried by the cap for relieving excessive pressure of the fluid in the reservoir and passage means mounted by the cap for establishing fluid communication through the annular chamber between the valve means and the reservoir without affecting said sealing fit, said passage means including an open inner tubular portion of the cap projecting axially through and beyond the annular chamber into the reservoir.

* * * * *